United States Patent [19]

Johnson

[11] Patent Number: 4,584,411
[45] Date of Patent: Apr. 22, 1986

[54] HYDROFORMYLATION PROCESS

[75] Inventor: Thomas H. Johnson, Houston, Tex.

[73] Assignee: Shell Oil Company, Houston, Tex.

[21] Appl. No.: 704,982

[22] Filed: Feb. 25, 1985

[51] Int. Cl.$^4$ .............................................. C07C 45/50
[52] U.S. Cl. .................................. 568/451; 568/454; 568/909
[58] Field of Search ....................... 568/451, 454, 909

[56] References Cited

U.S. PATENT DOCUMENTS

| | | | |
|---|---|---|---|
| 1,981,819 | 11/1934 | Wiezenich et al. | 568/951 |
| 3,255,259 | 6/1966 | Mertzweiller et al. | 568/451 |
| 3,937,742 | 2/1976 | Yoo | 568/451 |
| 3,965,192 | 6/1976 | Booth | 568/451 |
| 4,098,727 | 7/1978 | Haag et al. | 568/451 |

FOREIGN PATENT DOCUMENTS

| | | | |
|---|---|---|---|
| 0120543 | 7/1982 | Japan | 568/451 |
| 0021638 | 2/1983 | Japan | 568/451 |

Primary Examiner—Werren B. Lone

[57] ABSTRACT

This invention relates to a process for improving the hydroformylation of Dimersol oligomers by first contacting the catalyst with a tantalum (V) halide/oxide-inorganic oxide catalyst before hydroformylating.

6 Claims, No Drawings

HYDROFORMYLATION PROCESS

FIELD OF THE INVENTION

This invention relates to an improved hydroformylation process; particularly to an improved process for the hydroformylation of oligomers of propylene and butylene.

BACKGROUND OF THE INVENTION

Hydroformylation is a term used in the art to denote the reaction of an olefin with CO and $H_2$ to produce an aldehyde/alcohol which has one more carbon atom then the reactant olefin. Strictly speaking hydroformylation of an olefin produces an aldehyde. However, in many reaction processes the catalyst utilized to produce the aldehyde also reduces the aldehyde to the alcohol. In other cases a separate catalytic reduction step is utilized to reduce the aldehyde to the alcohol. Frequently, in the art, the term hydroformylation is utilized to cover the aldehyde and the reduction to the alcohol step in total, i.e., hydroformylation refers to the production of alcohols from olefins via carbonylation and an aldehyde reduction process. As used herein, hydroformylation refers to this production of alcohols as well as aldehydes from olefins.

The Dimersol Process is a catalyzed liquid phase oligomerization of lower olefins, particularly propylene and butylene. The catalyst is formed by reacting a nickel compound with a hydrocarbyl aluminum halide. The primary product is the dimer with smaller amounts of the trimer and tetramer being present. General discussion of the Dimersol Process can be found in *Hydrocarbon Processing*, Vol. 89, pp 143-149, May, 1980 and Vol. 91, pp 110-112, May, 1982. The higher oligomers are quite useful for converting to alcohols which can then be utilized as intermediates to produce detergent and lubricant products.

SUMMARY OF THE INVENTION

This invention relates to an improvement in the process for hydroformylating the olefin oligomer products from a Dimersol Process. The improvement comprises "enhancing" or "reforming" the olefin products from the Dimersol oligomerization of propylene and/or butylene by contracting said products with a tantalum (V) halide/oxide-inorganic oxide catalyst, separating out a $C_6$-$C_{12}$ product stream and then hydroformylating the stream. The catalytic enhancing of the olefin stream prior to hydroformylation results in a much higher hydroformylation rate and a higher product alcohol make when comparison is made to unenhanced olefin streams.

DESCRIPTION OF THE PREFERRED EMBODIMENTS

In this invention, a Dimersol oligomer product is contacted with a tantalum (V) halide/oxide-inorganic oxide catalyst, the resulting reformed olefins are fractionated into desired cuts ranging from $C_6$ to $C_{12}$ which are then hydroformylated to alcohols.

The Dimersol Process is a catalyzed liquid phase oligomerization, primarily dimerization, of propylene or butylene. The process was developed by the Institute Francais du Petrole. The process uses generally a catalyst prepared by reacting a nickel compound with a hydrocarbyl aluminum halide. Illustrations of the catalyst that can be used in this type of process are given in U.S. Pat. No. 4,366,087, issued Dec. 28, 1982, U.S. Pat. No. 4,326,650, issued Dec. 7, 1982 and U.S. Pat. No. 4,398,049, issued Aug. 9, 1983, all incorporated by reference herein. The Dimersol process produces primarily dimers with smaller amounts of trimers and tetramers as well as higher oligomers. An illustrative example of the products of this type of process is shown in Examples 6 and 10 of U.S. Pat. No. 4,398,049 wherein propylene and butylene are oligomerized to produce about 85% of the dimer, about 12% of the trimer and about 3% of the tetramer. In general, the product of the Dimersol oligomerization of propylene or butylene will result in a product comprising about 75-95% by weight of dimer, 9-15% by weight of trimer, 1-5% by weight of tetramer and less than 5% by weight of the higher oligomers.

The $C_6$-$C_{12}$ olefins present in the Dimersol oligomerization product can be hydroformylated to produce alcohols when can be used as suitable reactants to product valuable industrial products, such as, detergents and synthetic lubricants. However, the product direct from the Dimersol reactor contains a large number of isomers many of which are branched. This product hydroformylates relatively slowly. It has been found that by reacting the Dimersol product with the catalyst as hereinafter described which is a tantalum (V) halide/oxide-inorganic oxide material, the $C_6$-$C_{12}$ product cut of the Dimersol Process is "enhanced" for hydroformylation because the more highly branched materials are oligomerized out. The use of the tantalum (V) halide/oxide-inorganic oxide catalyst to "reform" or "enhance" the Dimersol product results in $C_6$, $C_8$, $C_9$ and $C_{12}$ olefins that hydroformylate relatively rapidly to alcohols with a higher alcohol yield.

The key to producing the compositions of the instant invention resides in the use of the tantalum (V) halide/oxide-inorganic oxide catalyst to reform the propylene and butylene oligomers to produce hexenes, octenes, nonenes and dodecenes which are more readily hydroformylated to alcohols. The exact chemical make-up of the reformed hexenes, octenes, nonenes and dodecenes are difficult if not impossible, to determine with conventional analytical techniques due to number of isomers present.

The catalysts used to prepare the composition of the instant invention comprise pentavalent tantalum (also written as tantalum (V)), halogen (or halide), oxygen (or oxide) and a solid inorganic oxide substrate wherein at least one valence of tantalum is bound to oxygen, which oxygen is bound to the substrate, at least one valence of the tantalum is bound to halogen and the remaining tantalum valences are bound to halogen and/or oxygen, which oxygen may or may not be bound to the substrate. The halogens are fluorine, chlorine, bromine, iodine and mixtures thereof. Preferred halogens are fluorine and chlorine.

The inorganic oxides that are useful as substrates to prepare the catalysts are those inorganic oxides which have hydroxyl groups attached to the surface of the substrate. The hydroxyl groups provide the means by which the tantalum pentahalides are bound by reaction to the surface of the substrate. The scope is broad and any metal or semi-metal oxides which have surface hydroxyl (or oxyhydroxyl) groups can be utilized in preparing the catalysts.

The term "inorganic oxide", although used herein in the singular tense, is meant to include the single oxides such as silica, or alumina as well as plural and complex oxides such as silica-alumina, silica-alumina-thoria, zeolites and clays. The term "semi-metal" is a term referring to the small-conductor materials like silicon, germanium etc., although in the catalyst art, the semi-metal oxides are frequently encompassed within the term "metal-oxide".

The preferred inorganic oxide substrates used to prepare the catalysts are the porous solid inorganic oxides which contain surface hydroxyl groups and which are conventionally used as catalysts and catalyst supports. Non-limiting examples of these types of materials include those having a major component of silica or alumina or both, such as, for example, alumina and aluminous materials, silica and siliceous materials; clays, particularly open lattice clays; and crystalline aluminosilicates (zeolites). Non-limiting examples of aluminous and siliceous materials include, for example, silica-alumina, silica-magnesia, silica-zirconia, silica-titania, alumina-chromia, alumina-ferric oxide, alumina-titania as well as ternary compositions such as, for example, silica-alumina-titania, silica-alumina-zirconia, etc. Non-limiting examples of crystalline alumino-silicates useful as substrates include synthetic zeolites, such as, for example, A, X, Y, L and ZSM types such as ZSM-5 and others and naturally occurring zeolites, such as, erionite, faujasite, mordenite, sodalite, cancrinite and others. Non-limiting examples of open lattice clays useful as substrates include bentonite, montmorillonite and others. In a preferred embodiment, the metal oxide should have a major component of silica or alumina or both.

Particularly suitable as substrates for preparing the catalysts are those solid inorganic oxide compositions known as metal or semi-metal oxide gels or gel oxides. The gel oxides which are particularly suitable for use in preparing the catalysts are any of the oxide gels that are well known in the catalytic art useful as either catalyst base materials or as supporting materials in catalyst compositions. Additionally, the term "metal or semi-metal oxide gel" or "gel oxide" as used herein shall also include the plural oxide gels, i.e., those that contain mixtures or compounds of two or more metal oxides. A metal or semi-metal oxide gel is basically a metal or semi-metal oxide that contains chemically bound water in the form of hydroxyl groups or oxyhydroxyl groups as opposed to adsorbed water and water of hydration, although adsorbed water and water of hydration may also be present. They are typically prepared by the precipitation of the metal or semi-metal component(s) in an aqueous medium. Upon calcination at sufficiently elevated temperatures, water is given off and the gel is converted to the oxide with two hydroxyl moieties giving one molecule of water and an oxygen is attached to a metal ion. Illustrative of gel oxide base materials used to prepare the catalysts are aluminas, silicas, alumina-silicas, alumina-zirconias, silica-zirconias and the like, including naturally occurring hydrous oxide materials such as clays, such as, for example, the kaolinites, the montmorillonites and the like. Among the clays the open lattice clays are particularly desirable. Also included are the zeolites, both natural and synthetic. The structure of the gel oxides can range from amorphous to highly crystalline. Preferred oxide gel materials are selected from the group consisting of alumina, silica, alumina-silica, crystalline alumino-silicates (zeolites) and open lattice clays.

Since the tantalum (V) halide/oxide is bound to the surface of the inorganic oxide substrate by a reaction of tantalum pentahalide with the inorganic oxide substrate through a hydroxyl moiety, the inorganic oxide substrate must have pendant surface hydroxyl groups attached to the surface. Before reaction, the inorganic oxide substrate must have pendant surface hydroxyl groups, whereas, after reaction, the inorganic oxide substrate may or may not have surface hydroxyl groups, depending on the degree of reaction with the tantalum pentahalide.

Prior to use in preparing the catalysts the hydroxyl-containing inorganic oxide substrate should be substantially free of absorbed water, i.e., "substantially dehydrated or anhydrous". The absorbed or free water is removed by heating the substrate at temperatures ranging from about 100° C. to about 900° C. prior to contact with the tantalum pentahalide vapor. Any environment that provides for drying is suitable such as air, vacuum, inert gas such as nitrogen, etc. The dried metal oxide substrate should be kept away from a humid atmosphere after drying. It is understood that a dried inorganic oxide substrate prior to use in preparing the catalysts will still contain chemically bound water in the form of hydroxide and oxyhydroxide.

An aluminum oxide gel is one of the preferred substrates. This alumina can be any of the variety of available aluminas. These are commercially available under various names such as alumina gels, activated aluminas, gamma aluminas, etc. Regarding purity of the alumina, it may be stated that small amounts of impurities are not generally detrimental, and may be beneficial when the impurity is present as a co-gel. In fact "impurities" may be purposely added for catalytic effects.

The following table lists several commercial aluminas and their properties which are found suitable.

| Alumina | Surface Area, m²/g | Pore Vol., cc/gm | Na, ppm | $SO_4^=$, % wt | $Fe_2O_3$, % wt | $Cl^-$, % wt |
|---|---|---|---|---|---|---|
| CCI[a] | 252 | 0.8 | 160 | 0.06 | — | 0.02 |
| KA-201[b] | 365 | 0.42 | 600 | 0.03 | — | 0.01 |
| RA-1[c] | 263 | 0.26 | 4700 | 0.02 | 0.18 | — |
| ACCO[d] | 225 | 0.68 | 580 | 0.6 | — | 0.6 |
| Norton | 218 | 0.62 | 51 | 0.03 | — | 0.03 |

[a]Catalysts & Chemicals, Inc., now United Catalysts
[b]Kaiser
[c]Reynolds Corporation
[d]American Cyanamid Corporation
[e]Conoco Corporation
[f]Filtrol Corporation Silica gel is also another preferred substrate. These are readily available commercially and are essentially substantially dehydrated amorphous silica. These materials are available in various density grades, from low density with surface areas ranging from about 100–300 m²/g to regular density with surface areas up to about 800 m²/g. The commercially available materials are used as dessicants, selective absorbents, catalysts and catalyst supports. Regarding purity of the silica, it may be stated that small amounts of impurities are not generally detrimental and may be beneficial when the impurity is present as a co-gel. In fact, "impurities" may be purposely added for catalytic effects. The following table lists several commercial silicas and their properties which are found suitable.

| Support | Surface Area, m²/g | Pore Vol., cc/g | Density g/cc | Particle Size |
|---|---|---|---|---|
| Davison* Grade 952 SiO₂ | 300 | 1.65 | 0.35 | 70 mesh |
| Davison Grade 59 SiO₂ | 300 | 1.15 | 0.38 | 8 mesh |
| Davison Grade 57 SiO₂ | 300 | 1.0 | 0.4 | 100 mesh |
| Davison Grade 12 SiO₂ | 700 | 0.54 | 0.75 | 20 mesh |
| Davison Grade 03 SiO₂ | 750 | 0.43 | 0.7 | 8 mesh (avg) |

*Manufactured by Davison Chemical Div., W. R. Grace & Co.

Other preferred substrates are the aluminosilicates. These materials contain various mixtures of aluminum and silicon oxides. They are readily available commercially and are generally employed as cracking catalysts. Typically they contain from about 50 to about 95, preferably from about 70 to about 90 percent by weight of silica. Illustrations of commercially available aluminasilicas are Davison Grade 980-25 (manufactured by Davison Chemical Division, W. R. Grace & Co.) which contains about 75% $SiO_2$ and 25% $Al_2O_3$ and Davison Grade 980-13 which contains about 87% $SiO_2$ and 13% $Al_2O_3$. These materials can be prepared in a conventional fashion, as for example by co-precipitation, co-gellation, or by spray drying.

Encompassed within the term "aluminosilicates" are most of the zeolites.

The zeolites are found to be specifically useful as substrates. Zeolites are ordered, porous crystalline aluminosilicates having a definite crystalline structure within which there are a large number of small cavaties which are interconnected by a number of still smaller channels. Zeolites useful as substrates may be either synthetic or natural. At least 34 species of zeolite minerals are known and the synthetic zeolites number in the hundreds. Any zeolite will be useful as a substrate provided that the zeolite, prior to reaction with tantalum pentahalide, contains chemically bound water in the form of hydroxyl groups. Depending on the state of reaction, the reacted product may contain no hydroxyl groups, if all such groups were reacted with the tantalum pentahalide, or there may be unreacted hydroxyl groups still present.

The techniques for the preparation of the tantalum pentahalide intermediates are well known in the art and typically are prepared by passing a dry halogen gas over tantalum metal at elevated temperatures. By way of illustration, tantalum pentachloride is prepared by passing dry chlorine over tantalum metal at a temperature above 200° C. The tantalum pentahalides utilized will comprise tantalum pentafluoride, tantalum pentachloride, tantalum pentabromide and tantalum pentiodide.

The gel oxide-tantalum (V) halide/oxide catalysts are prepared by a process comprising reacting under substantially anhydrous and oxygen-free conditions a suitable gel oxide which has water chemically bound as hydroxyl and which is substantially free from absorbed water with tantalum pentahalide vapor and thereafter recovering the product. The metal or semi-metal oxide catalysts thus produced have tantalum (V) halide/oxide bound to the surface thereof. By the term "bound" it is meant herein that the pentavalent tantalum has at least one valence bound to an oxygen which is part of the inorganic oxide substrate. By the term "surface" it is meant both the external and internal pore surfaces which are accessible to the tantalum pentahalide vapor during the preparative process.

The tantalum pentahalides readily sublime and thus lend themselves to a preferred method of preparation which is called "reactive sublimation" wherein tantalum pentahalide is sublimed into an anhydrous, non-oxidizing atmosphere and allowed to contact and react with the hydroxyl-containing metal or semi-metal oxide.

In the preparation of the catalysts, by reactive sublimation, it is important that the reaction be carried out under substantially anhydrous conditions and in a neutral or reducing environment to prevent decomposition of the tantalum halide.

In this preferred method of catalyst preparation, the tantalum pentahalide is sublimed by suitable application of temperature and/or vacuum into an essentially anhydrous and oxygen-free atmosphere where it is allowed to contact and react with a substantially anhydrous, hydroxyl-containing metal or semi-metal oxide substrate. Any temperature and/or vacuum which causes the tantalum pentahalide to sublime is suitable. Temperatures up to about 200° C. are suitable. Frequently the inorganic oxide substrate is heated during the reaction, say up to about 200° C. This heating is not critical to the preparation of catalysts, but it has been found that by so heating, a more even distribution of the tantalum pentahalide on the metal oxide substrate is effected. After reaction the inorganic oxide composition is frequently subjected to an additional period of time at sublimation conditions without the presence of a tantalum pentahalide source. This extra step allows for any unreacted tantalum pentahalide to be sublimed off of the metal or semi-metal oxide composition. The inorganic oxide substrate before use is frequently subjected to a heat treatment to remove absorbed water. Vacuum can also be applied. Generally, if the pre-treatment temperature is too low, free water will remain, and, if the temperature is too high, sintering of the inorganic oxide substrate will occur, both of which can adversely affect the catalytic properties. Generally, the most desirable pretreatment temperatures of the metal oxide substrate range from about 200° to about 400° C.

It is postulated that when tantalum pentahalide reacts with the hydroxyl group of a inorganic oxide substrate, that the reaction may be illustrated variously as follows (using chloride as an illustrative halide):

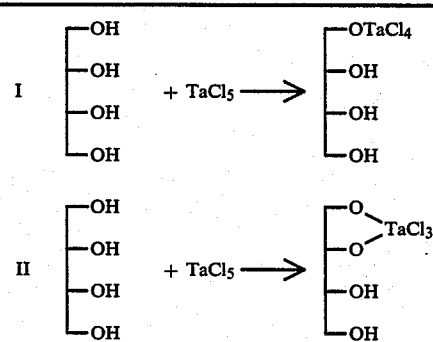

-continued

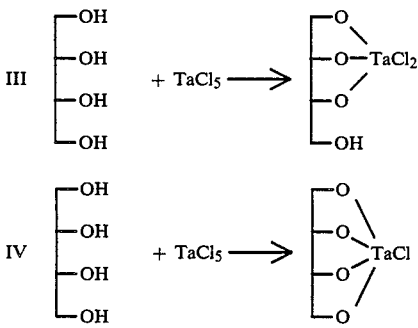

In the final catalyst a mixture of the above described reaction products will exist. The distribution of these reaction products is believed to be affected by reaction conditions, such as temperature. Analysis of chlorine/tantalum ratios in catalysts containing about 8–17% wt. of tantalum show Cl/Ta atomic ratios of from about 2.5:1 to about 3.5 to 1.

Thus, depending on the tantalum content desired in the final catalyst, a tantalum pentahalide vapor is reacted with the hydroxyl-containing metal or semi-metal oxide substrate until a part or the whole of the hydroxyl group population of the metal oxide substrate is exhausted.

The reaction between the tantalum pentahalide vapor and the hydroxyl-containing inorganic oxide substrate is carried out at temperatures ranging from about room temperature to elevated temperatures, say to 150°–200° C. or higher. The reaction is normally carried out in an anhydrous, i.e., free from water vapor, atmosphere. The atmosphere should further be a neutral or reducing atmosphere i.e., oxygen-free. Dispersal of the tantalum pentahalide vapor in a vacuum provides a quite suitable atmosphere for reaction with the metal or semi-metal oxide substrate.

The inorganic oxide-tantalum (V) halide/oxide catalysts may be produced in virtually any physical form, as for example, they may be pellets, beads, extrudates, microspheres and in other particular forms, as for example rings, saddles and the like and in porous or non-porous form.

The catalysts basically comprise metal or semi-metal oxide substrates having tantalum (V) halides/oxides reactively bound to the surface of said substrate. The halides are selected from the group consisting of fluoride, chloride, bromide, iodide and mixtures thereof. Preferred halides are fluoride and chloride. The catalysts are generally prepared by a process which comprises contacting the hydroxyl-containing metal or semi-metal oxide substrate in a substantially anhydrous state with tantalum pentahalide in the vapor state and allowing the vapor to react with the substrate in an atmosphere which is substantially oxygen- and water-free. In the preferred process sublimation of the tantalum pentahalide is used to put the tantalum pentahalide in the vapor state. Tantalum pentachloride is the preferred sublimation agent, producing the highest metal loadings on the inorganic oxide substrate.

A variation of the above process is utilized to produce a catalyst containing mixed halides, particular mixed chlorides and fluorides. In this variation a tantalum (V) chloride/oxide-inorganic oxide composition is prepared by reactive sublimation. The tantalum (V) chloride/oxide-metal oxide composition is then contacted with an oxygen-containing gas or a chemical compound containing oxygen which is weakly covalently bonded to the compound. It is postulated that oxygen replaces part of the halide of the composition. The material is then reacted with a liquid or gaseous fluorinated hydrocarbon which is believed to react preferentially with the oxygen bound only to the tantalum, producing, it is postulated, a composition containing various mixtures of chlorides, fluorides, oxides, oxychlorides, oxyfluorides, oxychlorofluorides, etc., depending on reaction conditions. Analyses of catalysts prepared in this fashion show that they contain varying amounts of chlorine and fluorine along with amounts of oxygen (not bound to the substrate) ranging from insignificant to moderate, depending on the degree of fluorination obtained using the fluorinated hydrocarbon. The amount of oxygen remaining can be varied by choice of fluorinated hydrocarbon and reaction conditions. Reaction temperatures and pressures for the reaction with the fluorinated hydrocarbon are not critical. Temperatures of room temperature or greater are generally suitable. Different fluorinated hydrocarbons will have different optimum temperatures, pressures and times of contact, and these can readily be determined by routine experimentation. Particularly suitable fluorinated hydrocarbons are the Freons, such as, for example Freon 12 ($CF_2Cl_2$), Freon 14 ($CF_4$), Freon 23 ($CHF_3$), Freon 112 ($CCl_2F$-$CCl_2F$), Freon 116 ($CF_3$-$CF_3$), Freon 142 (chlor-difluor-methyl methane), Freon C138 (octafluorocyclobutane) and similar materials. One particular advantage of this process is that it allows for the preparation of catalysts containing higher amounts of fluoride than does the process using reactive sublimation of tantalum pentafluoride alone. Compositions containing the fluoride are more resistant to oxygen degradation than the compositions containing chloride alone. Thus, when the mixed chloride/fluoride compositions are used as catalysts, the feeds need not be purged of oxygen and air is no longer a poison. Feeds containing oxygen (e.g., $O_2$, peroxide, etc.), however, will still compete for catalyst sites and, hence, the observed rates of reaction can be reduced.

As noted above, a modification of the basic catalyst can be obtained by contacting the tantalum (V) halide/oxide inorganic oxide compositions with oxygen or a compound containing oxygen which is weakly covalently bonded to said compound. Illustrative of said compounds are the peroxdes and peroxy compounds, both organic and inorganic, the hypohalide's etc. It is postulated that contact of the catalysts with oxygen or the indicated oxygen-containing compounds converts part of the halogen on the composition to oxygen which is not bound to the substrate. Thus, there are two possible types of oxygen bound to the pentavalent tantalum of the composition. One type is the oxygen(s) which is bound to the tantalum and to the substrate. This presence of this type of oxygen is required to produce the catalysts. The other type of oxygen which optionally may be present is oxygen bound only to the tantalum of the catalyst composition. Thus, at least one valence of pentavalent tantalum is bound to oxygen which is bound to the substrate, at least one valence of the tantalum is bound to halogen and the remaining tantalum valences are bound to halogen and/or oxygen which is or is not bound to the substrate. This modification containing the optional oxygen may be effected either inadvertently or purposefully. It may be effected by contact with oxygen or oxygen-containing compounds present as additives or impurities in feed streams when the compositions are used as catalysts.

The Dimersol product direct from the Dimersol reactor can be enhanced by contact with the tantalum (V) halide/oxide-oxide gel catalyst described herein using conventional techniques, such as a stirred reactor or a packed bed. The reaction temperature generally ranges from about 25° to about 300° C. preferably from about 100° to about 250° C.

Sufficient pressure is used to maintain most or all (at a least substantial portion) of the feed derived from the Dimersol process in the liquid state.

Pressures generally range from about 100 to about 1000 psi.

Alternatively, the Dimersol product from the Dimersol reactor may be fractionated into various cuts ranging from $C_6$ to about $C_{12}$, and these individual cuts are then contacted with the tantalum (V) halide/oxide-oxide gel catalyst.

After contact with the above-described tantalum (V) halide/oxide-inorganic oxide catalyst, the "reformed" or "enhanced" olefins are hydroformylated to alcohols and/or aldehydes. Preferably, however, the "reformed" olefins are separated, for example, by distillation, into narrow cuts with about a two carbon number spread before being hydroformylated. The hydroformylation of narrow cuts provides for easier processing of the product.

Hydroformylation is a term used in the art to denote the reaction of an olefin with CO and $H_2$ to produce and aldehyde/alcohol which has one more carbon atom than the reactant olefin. Strictly speaking hydroformylation of an olefin produces an aldehyde. However, in many reaction processes the catalyst utilized to produce the aldehyde also reduces the aldehyde to the alcohol. Frequently, in the art, the term hydroformylation is utilized to cover the aldehyde and the reduction to the alcohol step in total, i.e., hydroformylation refers to the production of alcohols from olefins via carbonylation and an aldehyde reduction process. As used herein, hydroformylation refers to this production of aldehydes/alcohols from olefins.

The hydroformylation step utilized in the instant process is not unique or critical to the instant invention. Any of the many well-known "oxo" hydroformylation processes can be utilized in the instant process. Various commercial processes have been summarized in SRI International's Progress Economics Program Reports, Report No. 27, Linear Higher Alcohols, August, 1967; Report No. 21, Oxo Alcohols, November, 1966; Report No. 21A, Oxo Alcohols, November, 1971; Report No. 21B, Oxo Alcohols, May, 1978. Further descriptions of the oxo can be found in "Organic Synthesis via Metal Carbonyls, Volume II" edited by I. Wender and P. Pino, John Wiley and Sons, 1977 and in "New Syntheses with Carbon Monoxide" (Reactivity and Structure Concepts in Organic Chemistry, Volume II), edited by J. Falbe, Springer-Verlag, 1980. These reports describe the use of various catalysts in a hydroformylation process as well as the detailed aspects of the process. Illustrative catalysts include cobalt hydrocarbonyl catalyst, cobalt-phosphine ligand catalyst, and rhodium-phosphine ligand catalyst. The choice of catalysts determines the various reaction conditions imposed. These conditions can vary widely, depending upon the particular catalysts. For example, temperatures can range from about room temperatures to about 300° C. When cobalt catalysts are used, temperatures will range from about 150° to about 250° C. One of ordinary skill in the art, by referring to the above-cited references, or any of the well-known literature on oxo alcohols can readily determine those conditions of temperature and pressure that will be needed to hydroformylate the reformed Dimersol product using the particular catalyst or catalysts involved.

After hydroformylation, the product alcohol/aldehydes can be separated from the hydroformylation product by conventional means such as for example, distillation.

The process of the instant invention is described below by the following illustrative embodiments which are provided for illustration, and are not to be construed as limiting the invention.

ILLUSTRATIVE EMBODIMENT

Catalyst Preparation

The following illustrates a typical preparation of the catalyst used to make the lubricants of the instant invention. Other examples are given in U.S. application Ser. No. 527,535 filed Aug. 29, 1983, now U.S. Pat. No. 4,489,171 issued Dec. 18, 1984, incorporated by reference herein. In this preparative technique, a glass scrubbing bottle was modified by internally adding a course fritted disc which divided the bottle into a upper section and a lower section. The lower section was fitted with a stoppered connection which allowed it to be charged with tantalum pentachloride and the upper section was fitted with a vacuum stopcock connection which allowed it either to be closed off or connected to a vacuum. To the modified gas-scrubbing bottle were added about 20 g of $TaCl_5$ to the bottom section and 60 g of Davison 57 silica ($-20+30$ mesh, pretreated at 300° C. under 0.1 torr vacuum for 12-24 h) to the top section. Both sections were loaded in a dry box containing a nitrogen atmosphere. The bottom section was stoppered and the top section had the vacuum stopcock before removing from the dry box. The bottom section of the bottle was immersed into an oil bath and heated at about 150° C. The top section was wrapped with heating tape and heated to about 150° C. A vacuum (about 0.1 torr) was applied at the top of the bottle. The heating and vacuum phase of the preparation was simultaneous and carried out over a period of 18 h. At the end of 18 h, the bottle (vacuum stopcock closed) was put back into the dry box and 20 g of fresh $TaCl_5$ was added to the bottom section. The rest of the procedure was then repeated for another 18 h. Then the silica was removed, in a nitrogen-filled dry box, and vertically sublimed at 150° C. and 0.1 torr for 18 h. This step was employed to remove any deposited but unreacted $TaCl_5$ on the silica surface. A small (<200 mg) of $TaCl_5$ was generally collected on the cold finger of the sublimator.

Twelve milliliters of the tantalum (V) chloride-silica composition was added to a fixed-bed flow reactor and treated with air at a flow rate of 4 liters/min for 15 minutes at 100 psi and 200° C. The air-treated material was then treated with Freon 12 ($CF_2Cl_2$) at 200° C. and 70 psi at a low rate of 2.4 liters/hr for 5 hours. The flow tube was then sealed and left under an atmosphere of Freon 12 at 200° C., 75 psi for 60 hours. Analysis of the resultant composition by neutron activation showed it to contain about 15.7 %w Ta, 1.9 %w Cl and 5.7 %w F.

Catalytic "Reformation" of Dimersol Oligomerization Product

A Dimersol feed-product containing about 82% hexenes, 12% nonenes and 6% higher oligomers was fed up-flow at a liquid hourly space velocity of about 5 h$^{-1}$ through a fixed-bed reactor containing 10 cc of the catalyst prepared similar to that described above (about 12.4 %w Ta) at about 200° C. and about 500 psig. A hexene product portion has separated from the about "reformed" product by distillation.

The above reformation process was repeated using a Dimersol feed-product containing about 85% octenes, 12% dodecenes and 3% higher oligomers. An octene product portion was separated from the above "reformed" product by distillation.

Hydroformylation of "Reformed" Dimersol Oligomerization Product

Hexenes and octenes from a Dimersol product, both unreformed (i.e., virgin) and reformed were hydroformylated in a series of comparative experiments.

The general conditions for the hydroformylations were as follows:

Hydroformylations were carried out in a 300 ml autoclave and stirred at 1250 rpm. The synthesis gas was 2.1:1.0H$_2$/CO. Reactions were run under a constant pressure of 1100 psig. Gas uptake was measured off of an auxillary vessel which had an initial pressure of 2100 psig and was used to maintain the 1100 psig pressure on the autoclave. The order of addition was: 110 g of hexene or octene, 0.84 g of 30% KOH/ETOH, 1.38 g of cobalt octoate, followed by 1.4 g of (n-Bu)$_3$P. The autoclave was flushed with nitrogen, filled to ca 900 psig with synthesis gas and heated to 175° C. (hexenes) or 185° C. (octenes). When the desired temperature was reached, the autoclave was pressurized to 1100 psig and maintained at that pressure to the end of the reaction (ca 21 h). Product analysis was performed by GC using an SP 2100 column at 70° C. (1 min hold) with a program rate of 5° C./min. Paraffin+olefin, alcohol, and heavies could be separated under these conditions. n-Heptane was used as an internal standard for alcohol content. Paraffin could be distinguished from olefin by ozonolysis and mass spectrometry.

Determination of the rate constants by gas uptake revealed that "reformed" C$_6$= hydroformylated 41% faster than virgin C$_6$=. "ReformedA" C$_8$= hydroformylated 35% faster than virgin C$_8$=. "Reformed" olefins made more alcohol than virgin olefins.

TABLE 1

| Feed | Rate (× 10$^3$ min$^{-1}$) | T, °C. | Conv. %$^a$ | Alcohol, % |
|---|---|---|---|---|
| Virgin C$_6$= | 1.7 | 175 | 97.5 | 75.2 |
| "Reformed C$_6$= | 2.4 | 175 | 98.1 | 78.2 |
| Virgin C$_8$= | 1.7 | 185 | 95.1 | 75.0 |
| "Reformed C$_8$= | 2.3 | 185 | 97.1 | 78.5 |

$^a$At 21 hours

I claim:

1. In a process for the hydroformylation of an olefin oligomerization product obtained by the liquid phase oligomerization of propylene and/or butylene in the presence of a catalyst formed by reacting a nickel compound with a hydrocarbyl aluminum halide, said hydroformylation being carried out by contacting said oligomerization product with syngas in the presence of a hydroformylation catalyst to produce aldehydes or alcohols, the improvement which comprises: contacting at a temperature ranging from about 25° C. to about 300° C. at least a portion of said oligomerization product with a reforming catalyst comprising pentavalent tantalum, halogen, oxygen and an inorganic oxide substrate wherein at least one valence of tantalum is bound to oxygen which is bound to the substrate, at least one valence of the tantalum is bound to halogen and the remaining tantalum valences are bound to halogen and/or oxygen which oxygen may or may not be bound to the substrate, and then hydroformylating the resultant olefin product to produce an alcohol or aldehyde.

2. The process of claim 1, where, in said reforming catalyst, the inorganic oxide substrate is silica, alumina, silica-alumina, zeolite, open lattice clay or mixtures thereof.

3. The process of claim 1, where, in said reforming catalyst, the inorganic oxide substrate has a major component of silica, or alumina or a mixture hereof and the halogen is chloride, fluoride or a mixture thereof.

4. The process of claims 1, 2 or 3 wherein, contact is made with the reforming catalyst at a temperature ranging from about 100° C. to about 250° C.

5. The process of claims 1, 2 or 3 wherein, prior to the hydroformylating, the reformed olefin product is separated into an olefin cut having a carbon number ranging from C$_6$ to C$_{12}$, which cut is then hydroformylated.

6. The process of claims 1, 2 or 3 wherein, prior to the hydroformylating, the reformed olefin product is separated into an olefin cut having a carbon number ranging from C$_6$ to C$_{12}$ with a carbon number spread at about two carbon atoms, which cut is then hydroformylated.

* * * * *